US010568497B2

(12) United States Patent
Nakagawa et al.

(10) Patent No.: US 10,568,497 B2
(45) Date of Patent: Feb. 25, 2020

(54) SIGNAL PROCESSING APPARATUS AND ENDOSCOPE SYSTEM WITH COMPOSITE IMAGE GENERATION

(71) Applicant: OLYMPUS CORPORATION, Tokyo (JP)

(72) Inventors: Hironori Nakagawa, Hachioji (JP); Tatsuhiko Suzuki, Hino (JP); Tomoki Iwasaki, Fuchu (JP); Susumu Hashimoto, Hachioji (JP); Toshihiro Hamada, Fuchu (JP); Yuji Kutsuma, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/800,178

(22) Filed: Nov. 1, 2017

(65) Prior Publication Data

US 2018/0049629 A1 Feb. 22, 2018

Related U.S. Application Data

(63) Continuation of application No. PCT/JP2016/053850, filed on Feb. 9, 2016.

(30) Foreign Application Priority Data

Sep. 18, 2015 (JP) .................................. 2015-185258

(51) Int. Cl.
*A61B 1/05* (2006.01)
*A61B 1/00* (2006.01)
*G02B 23/24* (2006.01)

(52) U.S. Cl.
CPC ............ *A61B 1/05* (2013.01); *A61B 1/00009* (2013.01); *G02B 23/2407* (2013.01);
(Continued)

(58) Field of Classification Search
CPC .. G02B 23/2407; G02B 27/1066; A61B 1/05; A61B 1/00009; A61B 1/00174;
(Continued)

(56) References Cited

U.S. PATENT DOCUMENTS 5,697,885 A * 12/1997 Konomura ........... H04N 1/2175
348/65
6,346,940 B1 * 2/2002 Fukunaga ............... G06T 15/20
345/420

(Continued)

FOREIGN PATENT DOCUMENTS

JP 2002200036 A 7/2002
JP 2003038432 A 2/2003
(Continued)

OTHER PUBLICATIONS

International Search Report dated May 17, 2016 issued in PCT/JP2016/053850.

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A first signal processing apparatus includes: an image processing unit configured to at least execute a composition process of generating composed image information in which first image information or second image information and textual information are superimposed; and a control unit configured to control the process of the image processing unit in accordance with communication with a second signal processing apparatus. The control unit selects either one of the first image information and the second image information, and when the second image information is selected, the control unit outputs a first command for instructing the second signal processing apparatus not to superimpose the second image information and the textual information (Continued)

related to the second image information, and causes the image processing unit to generate composite image information in which the second image information and the textual information related to the second image information are superimposed.

8 Claims, 12 Drawing Sheets

(52) U.S. Cl.
CPC ......... *A61B 1/0005* (2013.01); *A61B 1/00043* (2013.01); *A61B 1/00059* (2013.01); *A61B 1/00096* (2013.01); *G06T 2207/10068* (2013.01)

(58) Field of Classification Search
CPC ............ A61B 1/00177; A61B 1/00179; A61B 1/00181; A61B 1/00183; A61B 2090/364; A61B 2090/365; A61B 2090/368; A61B 5/7425; A61B 5/743; A61B 5/7435; A61B 2034/2065
USPC ........ 600/109, 110, 111, 112, 113, 117, 118, 600/160, 166, 170, 171, 176, 182
See application file for complete search history.

(56) References Cited

U.S. PATENT DOCUMENTS

| 6,422,994 | B1* | 7/2002 | Kaneko | A61B 1/00009 600/160 |
|---|---|---|---|---|
| 8,937,651 | B2* | 1/2015 | Guissin | G02B 13/06 348/239 |
| 2005/0148854 | A1* | 7/2005 | Ito | A61B 1/00149 600/407 |
| 2005/0203343 | A1* | 9/2005 | Kang | A61B 1/00009 600/160 |
| 2006/0025692 | A1* | 2/2006 | Ishihara | A61B 1/00096 600/478 |
| 2015/0145953 | A1* | 5/2015 | Fujie | G02B 23/2415 348/45 |
| 2015/0182107 | A1* | 7/2015 | King | A61B 1/05 600/473 |
| 2015/0235373 | A1* | 8/2015 | Kato | A61B 1/00009 348/51 |
| 2017/0020627 | A1* | 1/2017 | Tesar | A61B 90/20 |

FOREIGN PATENT DOCUMENTS

| JP | 2008023041 A | 2/2008 |
|---|---|---|
| JP | 2009039249 A | 2/2009 |

* cited by examiner

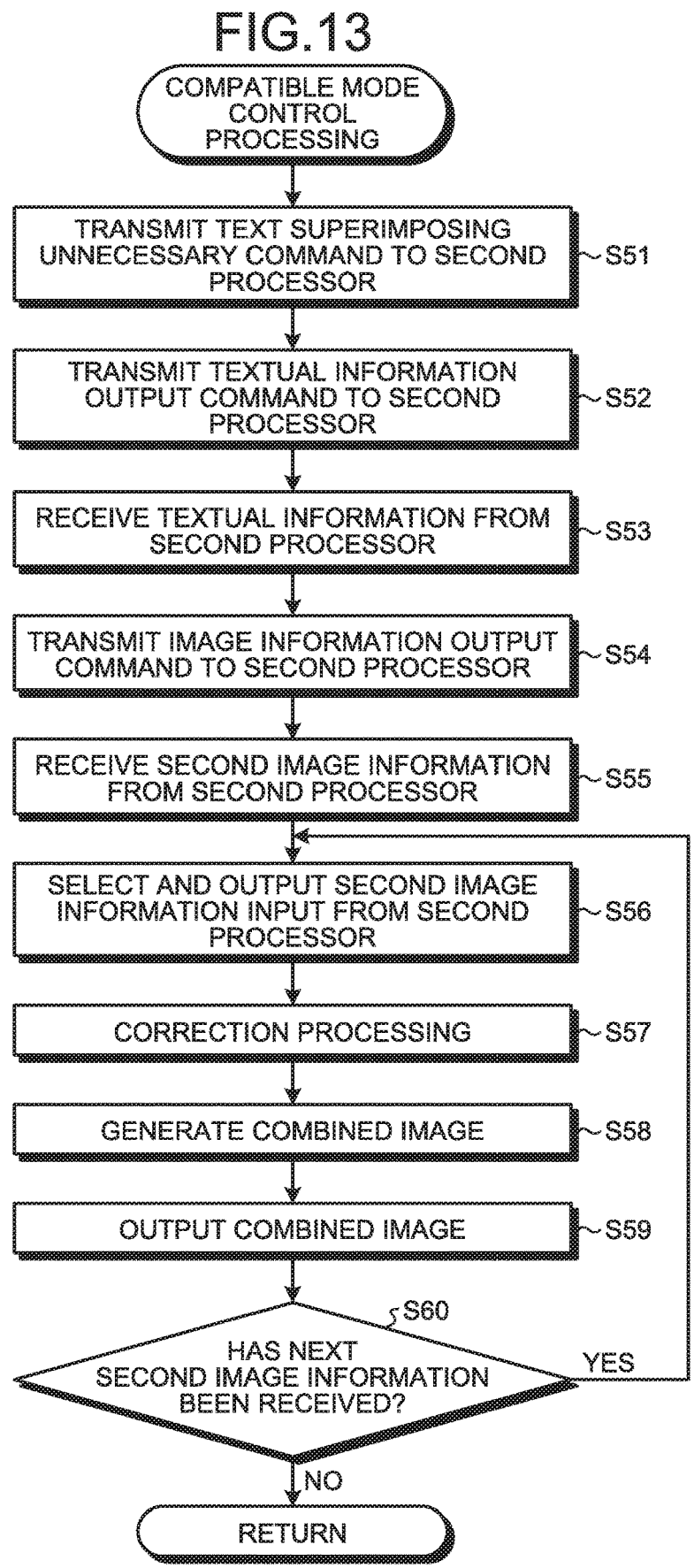

US 10,568,497 B2

SIGNAL PROCESSING APPARATUS AND ENDOSCOPE SYSTEM WITH COMPOSITE IMAGE GENERATION

CROSS-REFERENCE TO RELATED APPLICATION

This application is a continuation of PCT international application Ser. No. PCT/JP2016/053850 filed on Feb. 9, 2016 which designates the United States, incorporated herein by reference, and which claims the benefit of priority from Japanese Patent Applications No. 2015-185258, filed on Sep. 18, 2015, incorporated herein by reference.

BACKGROUND

The present disclosure relates to a signal processing apparatus and an endoscope system.

In the medical field, an endoscope system is used for observing internal portions of a subject. The endoscope typically inserts an insertion unit having a thin and long shape into a subject such as a patient, emits illumination light supplied by a light source apparatus from a distal end of the insertion unit, and receives reflected light of the illumination light by an image sensor, thereby capturing an in-vivo image. The in-vivo image captured by the image sensor of the endoscope undergoes predetermined image processing by a signal processing apparatus (processor) of the endoscope system, and thereafter is displayed on a display of the endoscope system. A user such as a doctor observes an internal organ of the subject based on the in-vivo image displayed on the display.

In endoscopic inspection, since various endoscopes are appropriately used in accordance with the purpose of observation and an observed region, a plurality of endoscopes is used in combination in some cases. An endoscope system includes a processor, a display, and a recording apparatus as a set for individual types of endoscopes. Therefore, in a case of using a plurality of endoscopes in combination, a plurality of sets of processors, displays, and recording apparatuses is installed in accordance with each of the endoscopes. This results in complication of a wiring structure among the apparatuses and a necessity to ensure a wide area for installation, leading to enlargement of the entire system. In order to simplify the configuration of the entire system, there is a proposed configuration in which two processors are connected to each other, and one of the processors performs as a parent device output of image information to a display or a recording apparatus, thereby sharing the display or the recording apparatus by a plurality of processors (for example, refer to JP 2003-038432 A).

SUMMARY

According to one aspect of the present disclosure, there is provided a first signal processing apparatus to which a first endoscope apparatus including a first image sensor is detachably attached, the first signal processing apparatus being communicably connected to a second signal processing apparatus to which a second endoscope apparatus including a second image sensor is attached, and being configured to process an imaging signal generated by one of the first image sensor and the second image sensor, the first signal processing apparatus including: an image processing unit configured to at least execute a composition process of generating composed image information in which first image information based on the imaging signal generated by the first image sensor of the first endoscope apparatus or second image information input from the signal processing apparatus based on the imaging signal generated by the second image sensor of the second endoscope apparatus and textual information related to the first image information or to the second image information are superimposed; and a control unit configured to control the process of the image processing unit in accordance with communication with the second signal processing apparatus, wherein the control unit selects either one of the first image information and the second image information, and when the second image information is selected, the control unit outputs a first command for instructing the second signal processing apparatus not to superimpose the second image information and the textual information related to the second image information, and causes the image processing unit to generate composite image information in which the second image information and the textual information related to the second image information are superimposed.

According to another aspect of the present disclosure, there is provided an endoscope system including: a first signal processing apparatus to which a first endoscope apparatus including a first image sensor is detachably attached; and a second signal processing apparatus to which a second endoscope apparatus including a second image sensor is attached, wherein the first signal processing apparatus and the second signal processing apparatus are communicably connected to each other, and the endoscope system performs signal processing on an image signal generated by the first image sensor or by the second image sensor, and wherein the first signal processing apparatus includes: an image processing unit configured to at least execute a composition process of generating composed image information in which first image information based on the imaging signal generated by the first image sensor of the first endoscope apparatus or second image information input from the signal processing apparatus based on the imaging signal generated by the second image sensor of the second endoscope apparatus and textual information related to the first image information or to the second image information are superimposed; and a control unit configured to control the process of the image processing unit in accordance with communication with the second signal processing apparatus, wherein the control unit selects either one of the first image information and the second image information, and when the second image information is selected, the control unit outputs a first command for instructing the second signal processing apparatus not to superimpose the second image information and the textual information related to the second image information, and causes the image processing unit to generate composite image information in which the second image information and the textual information related to the second image information are superimposed.

The above and other objects, features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 13 is a flowchart illustrating a processing procedure of the compatible mode control processing by the control unit of the first processor illustrated in FIG. 12.

DETAILED DESCRIPTION

Figure 1:
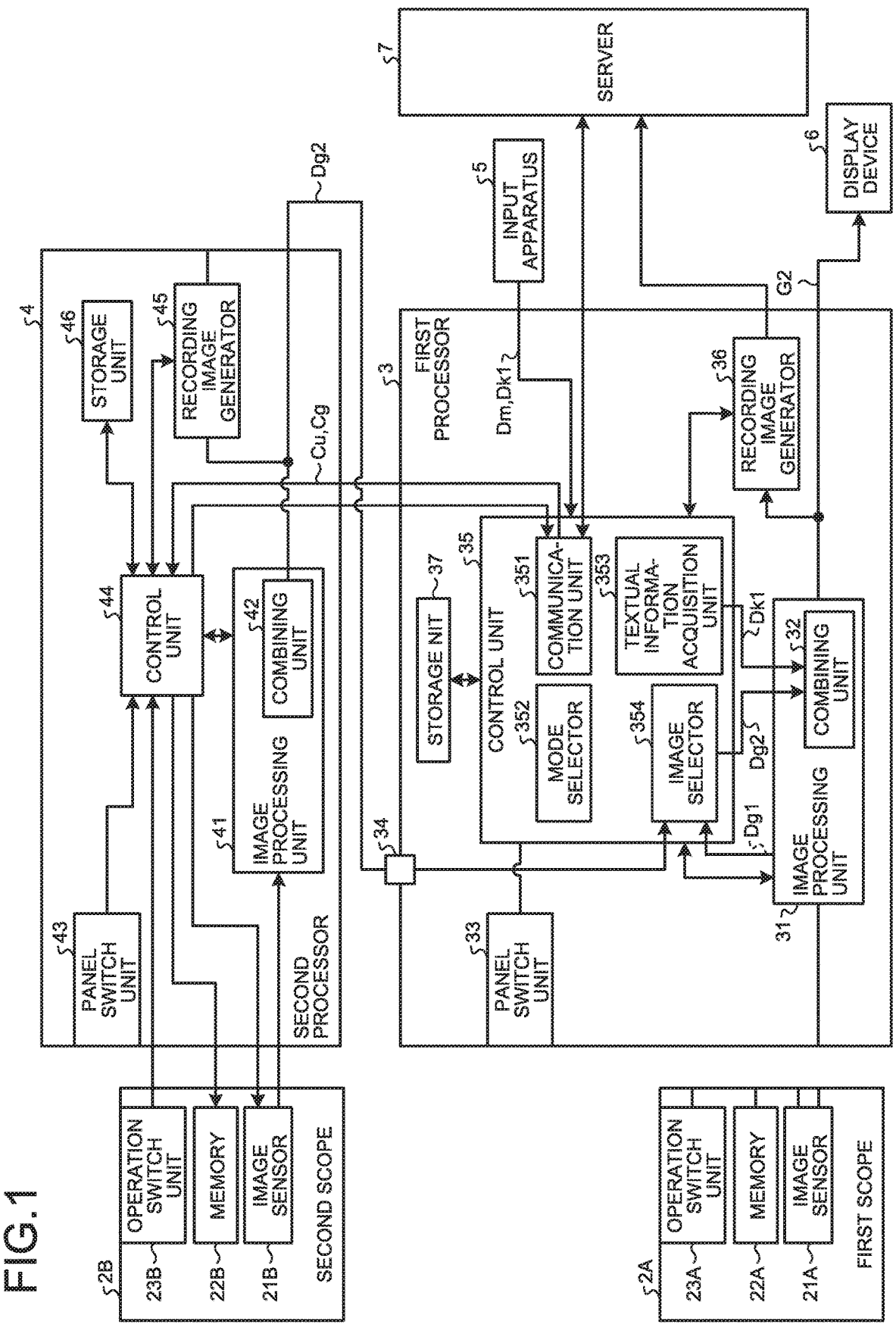
FIG. 1 is a schematic diagram illustrating a general configuration of an endoscope system according to a first embodiment of the present disclosure.

Hereinafter, a signal processing apparatus (processor) of an endoscope system will be described according to embodiments of the present disclosure (hereinafter, referred to as "embodiment(s)"). Note that the present disclosure is not intended to be limited by these embodiments. In the drawings, same reference signs are attached to the same portions.

First Embodiment

FIG. 1 is a schematic diagram illustrating a general configuration of an endoscope system according to a first embodiment of the present disclosure.

As illustrated in FIG. 1, the endoscope system according to the first embodiment uses, as an endoscope (scope) to be introduced into a subject, a first scope 2A attachable to a first processor 3 (signal processing apparatus, first signal processing apparatus) or a second scope 2B attachable to a second processor 4 (another signal processing apparatus, second signal processing apparatus), for example. The endoscope system according to the first embodiment includes the first processor 3, the second processor 4, an input apparatus 5, a display device 6, and a server 7. The first processor 3 performs predetermined image processing on an imaging signal transmitted from the attached first scope 2A. The second processor 4 performs predetermined image processing on an imaging signal transmitted from the attached second scope 2B. The input apparatus 5 receives an input of various types of instruction information and inputs the received instruction information into the first processor 3. The display device 6 displays a video image corresponding to an imaging signal obtained by one of the first scope 2A and the second scope 2B. The server 7 is connected to and communicates with the first processor 3 via a network, or the like, and records various types of information. In the first embodiment, the first processor 3 is communicably connected with the second processor 4 to which the second scope 2B is attached, and also is connected to the input apparatus 5 and the display device 6. The first processor 3 controls image processing including a composition process in the first processor 3 according to communication with the second processor 4, thereby generating a composed image from which necessary information may be sufficiently read as a composed image in which textual information is superimposed on image information, input from the second processor 4.

Each of the first scope 2A and the second scope 2B is introduced into the subject and generates image information of an internal portion of the subject by imaging the internal portion of the subject. The first scope 2A is connected to the first processor 3, and the second scope 2B is connected to the second processor 4.

The first scope 2A includes, at its distal end portion, an image sensor 21A (first image sensor), a memory 22A, and an operation switch unit 23A including various operation switches such as a release button. The second scope 2B includes, at its distal end portion, an image sensor 21B (second image sensor), a memory 22B, and an operation switch unit 23B including various operation switches such as a release button.

Examples of the image sensors 21A and 21B include a CCD image sensor and a CMOS image sensor. A light receiving surface of the image sensor includes a plurality of pixels arranged in a matrix. Each of the pixels receives light from the subject onto which light is emitted and generates an imaging signal by photoelectrically converting the received light. In a case where the first scope 2A is attached to the first processor 3, the image sensor 21A performs noise reduction processing, clamp processing, and A/D conversion processing onto a first imaging signal (analog) generated by the plurality of pixels, and outputs the signal as a first imaging signal (digital) to the first processor 3 via an electric cable (not illustrated). In a case where the second scope 2B is attached to the second processor 4, the image sensor 21B performs noise reduction processing, clamp processing, and A/D conversion processing onto a second imaging signal (analog) generated by the plurality of pixels, and outputs the signal as a second imaging signal (digital) to the second processor 4 via an electric cable (not illustrated).

The memories 22A and 22B record the identification information and the model numbers of the scopes 2A, and 2B, the type of the image sensors 21A and 21B, or the like. The memories 22A and 22B may record various parameters for image processing on the imaging signals captured by the image sensors 21A and 21B, such as parameters for white balance (WB) adjustment. In a case where the first scope 2A is attached to the first processor 3, the various types of information recorded by the memory 22A is output to a control unit 35 of the first processor 3 by communication processing with the first processor 3 via an electric cable (not illustrated). In a case where the second scope 2B is attached to the second processor 4, the various types of information recorded by the memory 22B is output to a control unit 44 of the second processor 4 by communication processing with the second processor 4 via an electric cable (not illustrated).

Each of the operation switch units 23A and 23B includes a plurality of buttons for operating the first processor 3 and peripheral equipment such as an air supply apparatus, a water supply apparatus, and a gas supply apparatus. Each of the operation switch units 23A and 23B includes a release button. In a case where the release button is pressed during scope inspection, each of the operation switch units 23A and 23B inputs a release signal into the control units 35 and 44 of each of the processors 3 and 4. The release signal instructs generation of still image data (release image data) from the image displayed on the display device 6 in a case where the release button is pressed. In accordance with the input of the release signal, each of recording image generators 36 and 45 to be described below generates release image data based on the video image displayed on the display device 6 at the input timing of the release signal. A bending knob for bending the first scope 2A and the second scope 2B and an insertion port for inserting a treatment instrument are provided in the vicinity of the operation switch units 23A and 23B.

The first scope 2A is detachably attached to the first processor 3. An image processing unit 31 to be described below generates first image information Dg1 by performing predetermined image processing on the first imaging signal transmitted from the attached first scope 2A. The first processor 3 is also communicably connected with the second processor 4. The first processor 3 transmits various commands to the control unit 44 of the second processor 4. The first processor 3 selects one of the first image information Dg1 generated by the image processing unit 31 and second image information Dg2 input from the second processor 4, and then, generates a composed image by superimposing the selected image information and textual information related to the image information, and outputs the composed image to the display device 6. The first processor 3 generates recording image information from the generated composed image and outputs the generated information to the server 7. The first processor 3 includes an image processing unit 31, a panel switch unit 33, an external video image input port 34, the control unit 35, a recording image generator 36, and a storage unit 37.

The image processing unit 31 performs predetermined image processing on the first imaging signal generated by the image sensor 21A of the first scope 2A. The image processing unit 31 generates the first image information Dg1 by performing optical black subtraction (OB) processing, demosaicing processing, white balance (WB) adjustment processing, electronic zoom processing, edge enhancement processing, mask processing on the first imaging signal (digital) generated by the image sensor 21A. The image processing unit 31 outputs the generated first image information Dg1 to an image selector 354 to be described below. The image processing unit 31 includes a composing unit 32, converts the composed image (composed image information) generated by the composing unit 32 into a format that may be displayed on the display device 6, and outputs the converted image. Note that there is a case where the image processing unit 31, instead of the image sensor 21A, performs noise reduction processing, clamp processing, and A/D conversion processing on the first imaging signal (analog).

The composing unit 32 executes on-screen display (OSD) processing, that is, processing of generating a composed image by superimposing image information that has undergone predetermined image processing and textual information related to the image information. The textual information is information indicating patient information, device information, examination information, or the like. The composing unit 32 generates a composed image by superimposing the image information input from the image selector 354 to be described below and the textual information related to the image information. In a case where the first image information Dg1 is input, the composing unit 32 generates a composed image by superimposing the first image information Dg1 and the textual information. In a case where the second image information Dg2 is input, the composing unit 32 generates a composed image by superimposing the second image information Dg2 and the textual information.

The panel switch unit 33 is a switch group provided on a front panel constituting a casing of the first processor 3. In a case where the first scope 2A is attached to the first processor 3, the panel switch unit 33 receives an input of signals for freeze, release, and image adjustment (emphasis, electronic enlargement, color tone, etc.) onto the in-vivo image captured by the first scope 2A, and outputs the received various signals to the control unit 35.

The second image information Dg2 output from an image processing unit 41 of the second processor 4 is input into the external video image input port 34 when the first processor 3 is connected with the second processor 4. The input second image information Dg2 is output to the control unit 35. The second image information Dg2 is obtained by performing predetermined image processing on the second imaging signal generated by the image sensor 21B of the second scope 2B and the textual information is not superimposed in the second image information Dg2.

The control unit 35 includes a CPU. The control unit 35 controls processing operation of each of portions of the first processor 3 by performing operation including transfer of instruction information and data to each of components of the first processor 3. In a case where the first scope 2A is attached to the first processor 3, the control unit 35 is connected to the image sensor 21A and the memory 22A of the first scope 2A via individual cables, and controls the image sensor 21A and the memory 22A.

The control unit 35 is communicably connected to the server 7 via a network, or the like. The control unit 35 is communicably connected to the control unit 44 of the second processor 4 via a cable. The control unit 35 controls processing of the image processing unit 31 according to communication with the second processor 4. The control unit 35 includes a communication unit 351, a mode selector 352, a textual information acquisition unit 353, and an image selector 354.

The communication unit 351 communicates with the control unit 44 of the second processor 4. In a case where communication with the second processor 4 is established, the communication unit 351 transmits a text superimposing unnecessary command (first command) Cu indicating non-execution of superimposing of textual information on the second image information Dg2, and transmits an image information output command (second command) Cg indicating transmission of the second image information Dg2 to the first processor 3, to the image processing unit 41 via the control unit 44 of the second processor 4 to be described below.

In accordance with the communication with the second processor 4 in the communication unit 351, the mode selector 352 selects any of a standard mode and a compatible mode. As image information composed by the composing unit 32, the first image information Dg1 generated by the image sensor 21A of the first scope 2A is selected in the standard mode, and the second image information Dg2 input from the second processor 4 is selected in the compatible mode. The mode selector 352 selects the compatible mode in a case where the second scope 2B connected to the second processor 4 is selected and communication is established between the communication unit 351 and the second processor 4. In a case where the first scope 2A connected to the first processor 3 is selected, the mode selector 352 selects the standard mode of superimposing the first image information Dg1 obtained by performing image processing on the first imaging signal generated by the image sensor 21A inside the first processor 3, and the textual information. The mode selector 352 controls the image processing unit 31 so as to perform image processing corresponding to the selected mode. The mode selector 352 causes the composing unit 32 of the image processing unit 31 to generate a composed image by superimposing the image information selected by the image selector 354 described below and the textual information related to the image information.

The textual information acquisition unit 353 obtains textual information related to the image information input from the input apparatus 5 described below. When the first scope 2A is attached, the textual information acquisition unit 353 obtains textual information related to the first image information Dg1. When the second scope 2B is attached, the textual information acquisition unit 353 obtains textual information related to the second image information Dg2.

The image selector 354 selects any one of the first image information Dg1 based on the first imaging signal generated by the image sensor 21A and the second image information Dg2 based on the second imaging signal generated by the image sensor 21B input from the second processor 4 corresponding to the mode selected by the mode selector 352. In a case where the mode selector 352 selects the standard mode, the image selector 354 selects the first image information Dg1 input from the image processing unit 31 and outputs the selected information to the composing unit 32. In a case where the mode selector 352 selects the compatible mode, the image selector 354 selects the second image information Dg2 input from the second processor 4 and outputs the selected information to the composing unit 32. The image selector 354 selects the second image information Dg2 input from the second processor 4 in accordance with the image information output command Cg transmitted by the communication unit 351 to the second processor 4.

The recording image generator 36 generates release image information and moving image information for recording by performing codec processing on the image information output from the image processing unit 31. Upon receiving a moving image generation instruction signal from the control unit 35, the recording image generator 36 generates (by encoding) moving image information of a predetermined format from a series of continuous image information output from the image processing unit 31 and outputs the generated information to the server 7. Upon receiving a release signal from the control unit 35, the recording image generator 36 generates release image data from the image information output from the image processing unit 31, and outputs the generated release image data to the server 7. In a case where the mode selector 352 selects the standard mode, the image processing unit 31 outputs a composed image based on the first image information Dg1. Accordingly, the recording image generator 36 generates recording image information such as moving image data or release image data based on the composed image information. In a case where the mode selector 352 selects the compatible mode, the image processing unit 31 outputs a composed image G2 based on the second image information Dg2. Accordingly, the recording image generator 36 generates recording image information such as moving image data or release image data based on the composed image G2.

The storage unit 37 includes a volatile memory and a non-volatile memory, and stores various programs for operating the first processor 3. The storage unit 37 temporarily stores the information being processed by the first processor 3. The storage unit 37 stores the first imaging signal output from the first scope 2A. The storage unit 37 may also be formed with a memory card, or the like, attached from outside of the first processor 3.

The second scope 2B is detachably attached to the second processor 4. The second processor 4 generates the second image information Dg2 obtained by performing predetermined image processing on the second imaging signal transmitted from the attached second scope 2B. The second processor 4 is communicably connected to the first processor 3 and inputs the generated second image information Dg2 into the external video image input port 34 of the first processor 3. The second processor 4 includes the image processing unit 41, a panel switch unit 43, the control unit 44, a recording image generator 45, and a storage unit 46.

The image processing unit 41 performs predetermined image processing on the second imaging signal generated by the image sensor 21B of the second scope 2B. Similarly to the image processing unit 31, the image processing unit 41 generates the second image information Dg2 by performing optical black subtraction (OB) processing, demosaicing processing, white balance (WB) adjustment processing, electronic zoom processing, edge enhancement processing, mask processing, or the like, on the second imaging signal (digital) generated by the image sensor 21B. The image processing unit 41 includes a composing unit 42 that performs OSD processing. The OSD processing in the composing unit 42 is not executed under the control of the control unit 44 in some cases. Note that, in some cases, the image sensor 21B of the second scope 2B performs processing up to the noise reduction processing, clamp processing, and A/D conversion processing, and outputs the second imaging signal (digital). In a case where the second processor 4 is used as a standalone unit, the image processing unit 41 converts a composed image in which the second image information Dg2 and textual information are superimposed into a format that may be displayed on a display device (not illustrated) included as a set with the second processor 4 and outputs the converted composed image.

The panel switch unit 43 is a switch group provided on a front panel constituting a casing of the second processor 4. In a case where the second scope 2B is attached to the second processor 4, the panel switch unit 43 receives an input of signals for freeze, release, and image adjustment (emphasis, electronic enlargement, color tone, etc.) onto the in-vivo image captured by the second scope 2B, and outputs the received various signals to the control unit 44.

Similarly to the control unit 35, the control unit 44 includes a CPU and controls processing operation of each of portions of the second processor 4 by performing operation including transfer of instruction information and data to each of components of the second processor 4. In a case where the second scope 2B is attached to the second processor 4, the control unit 44 is connected to the image sensor 21B and the memory 22B of the second scope 2B via individual cables, and controls the image sensor 21B and the memory 22B. The control unit 44 is communicably connected to the control unit 35 of the first processor 3 via a cable. The control unit 44 controls processing of the image processing unit 41 in accordance with the text superimposing unnecessary command Cu and the image information output command Cg transmitted from the control unit 35.

The recording image generator 45 includes the similar function as the recording image generator 36. Note that in a case where the second processor 4 is communicably connected with the first processor 3 and the compatible mode is selected in the first processor 3, the recording image generator 36 in the first processor 3 generates a release image information or a moving image information from the second image information Dg2. Accordingly, the recording image generator 45 does not execute generation processing of the release image information or the moving image information.

Similarly to the storage unit 37, the storage unit 46 is formed with a volatile memory, a nonvolatile memory, or the like, and stores various programs needed to operate the second processor 4 and the second imaging signal output from the second scope 2B, and in addition, temporarily stores information being processed by the second processor 4. The storage unit 46 may also be formed with a memory card, or the like, attached from outside of the second processor 4.

The input apparatus 5 includes an operation device such as a mouse, a keyboard and a touch panel. The input apparatus 5 receives input of various types of instruction information and inputs the received various types of instruction information to the control unit 35 of the first processor 3. In a case where the first processor 3 and the second processor 4 are communicably connected with each other, it receives input of instruction information toward the second processor 4 and toward the second scope 2B attached to the second processor 4, and inputs the received instruction information to the control unit 35, in addition to the various types of instruction information toward the first processor 3. Moreover, the input apparatus 5 inputs into the control unit 35 scope selection information Dm indicating that either the first scope 2A or the second scope 2B has been selected as the scope to be used, and textual information Dk1 related to the image information as a composition process target by the composing unit 32.

The display device 6 is configured with a display using a liquid crystal or organic EL. The display device 6 displays various types of information including the display image output from the first processor 3. In the case of the standard mode, the display device 6 displays a composed image in which the first image information Dg1 based on the first imaging signal of the first scope 2A and the textual information related to the first image information Dg1 are superimposed. In the case of the compatible mode, the display device 6 displays a composed image G2 in which the second image information Dg2 based on the second imaging signal of the second scope 2B and the textual information related to the second image information Dg2 are superimposed. With this configuration, the user may observe a desired position inside the subject and judge conditions by operating the first scope 2A and the second scope 2B while viewing an image (in-vivo image) displayed by the display device 6. Note that, under the control of the control unit 35, the display of the display device 6 also displays information indicating whether the actually displayed in-vivo image is obtained by the first scope 2A or the second scope 2B.

The server 7 is connected with the first processor 3 via a network, or the like, and communicates with the first processor 3. The server 7 includes a database (not illustrated), and records and manages various types of information including identification information of the release image information, the moving image information, and the image signals output by the first processor 3, in a database.

Figure 2:
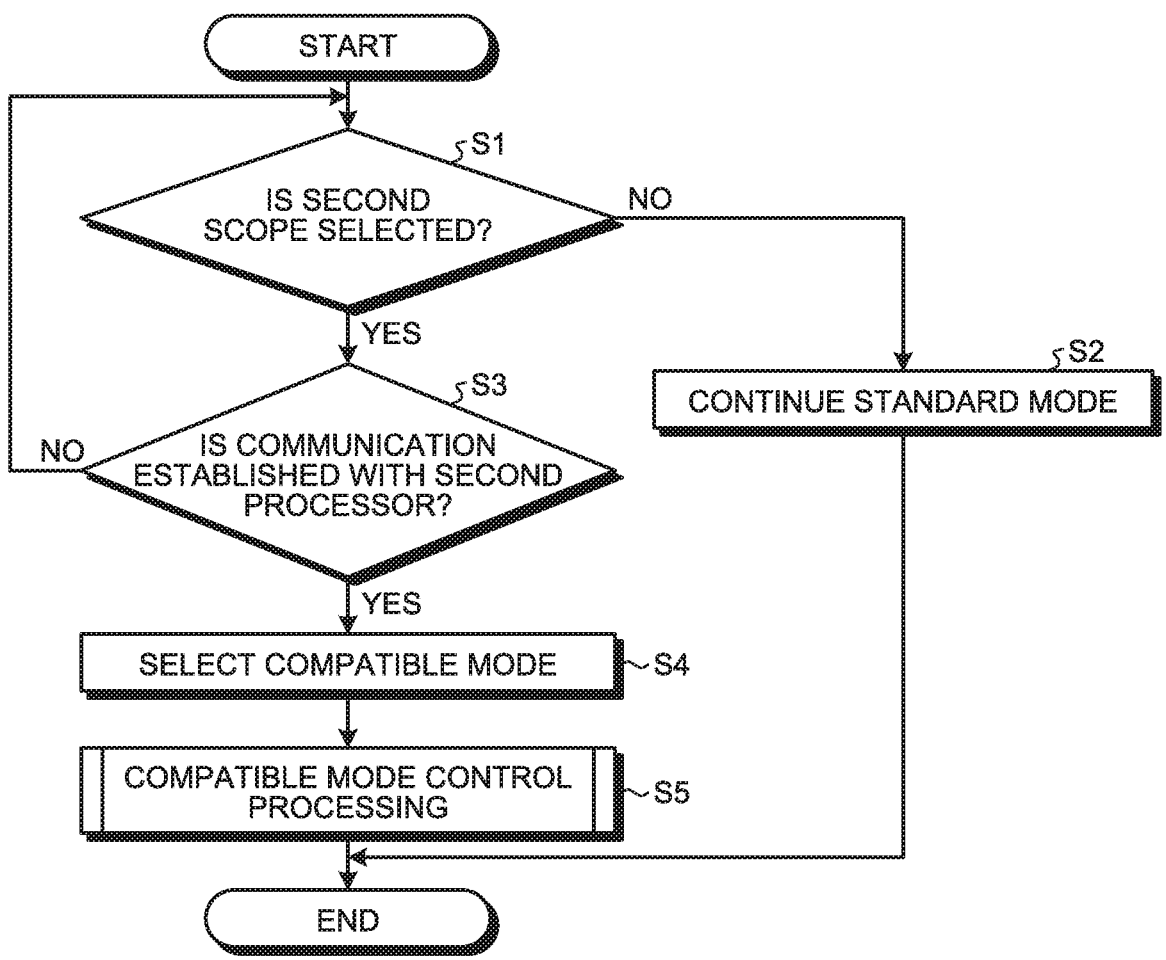
FIG. 2 is a flowchart illustrating setting of a standard mode or a compatible mode by a control unit of a first processor illustrated in FIG. 1 and a processing procedure of control processing of internal processing of the first processor in accordance with individual modes.

FIG. 2 is a flowchart illustrating setting of the standard mode or the compatible mode by the control unit 35 of the first processor 3 and a processing procedure of control processing of internal processing of the first processor 3 in accordance with individual modes. In the first processor 3, the standard mode is set as the default mode.

As illustrated in FIG. 2, the control unit 35 determines whether the second scope 2B has been selected as the scope to be used based on the scope selection information Dm, or the like, input from the input apparatus 5 (Step S1). In a case where the control unit 35 determines that the second scope 2B is not selected (Step S1: No), the mode selector 352 continues the standard mode (Step S2).

In contrast, in a case where the control unit 35 determines that the second scope 2B is selected (Step S1: Yes), the control unit 35 determines whether communication is established between the first processor 3 and the second processor 4 based on communication results on the communication unit 351 (Step S3). In a case where the control unit 35 determines that communication is not established between the first processor 3 and the second processor 4 (Step S3: No), the control unit 35 returns to Step S1, and determines whether the second scope 2B is selected.

In a case where the control unit 35 determines that communication is established between the first processor 3 and the second processor 4 (Step S3: Yes), the mode selector 352 selects the compatible mode (Step S4), and the control unit 35 performs compatible mode control processing of controlling the image processing unit 31 so as to correspond to the compatible mode (Step S5).

Figure 3:
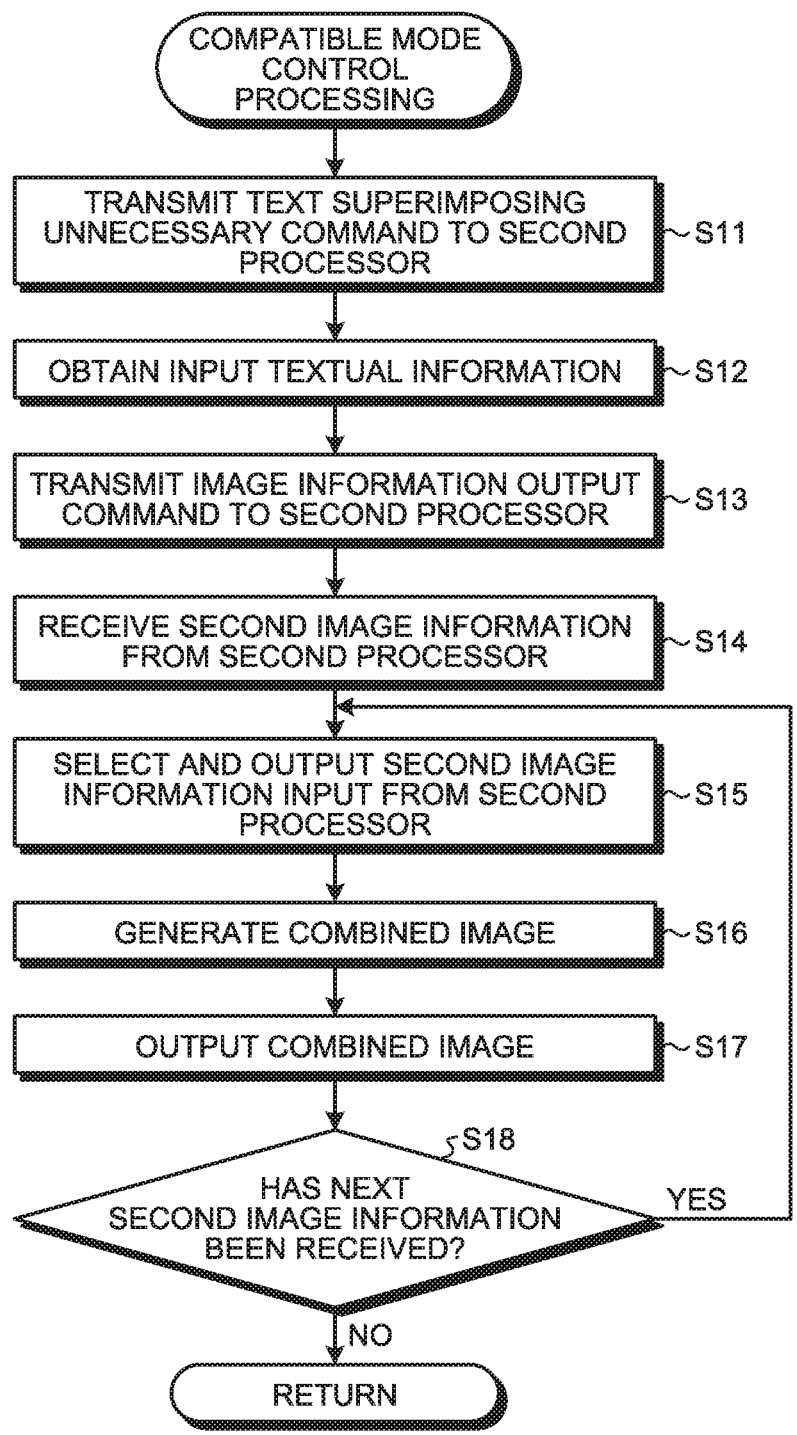
FIG. 3 is a flowchart illustrating a processing procedure of compatible mode control processing illustrated in FIG. 2.

FIG. 3 is a flowchart illustrating a processing procedure of the compatible mode control processing illustrated in FIG. 2. As illustrated in FIG. 3, the communication unit 351 transmits the text superimposing unnecessary command Cu to the second processor 4 (Step S11). In the second processor 4, the OSD processing in the composing unit 42 is not executed in response to reception of the text superimposing unnecessary command Cu. The textual information acquisition unit 353 obtains the textual information Dk1 input from the input apparatus 5 (Step S12) and outputs the obtained information to the composing unit 32.

The communication unit 351 transmits the image information output command Cg to the second processor 4 (Step S13). In response to the reception of the image information output command Cg, the second processor 4 outputs the second image information Dg2 in a state where textual information is not superimposed from the image processing unit 41, and then, the control unit 35 receives the second image information Dg2 output from the second processor 4 (Step S14) via the external video image input port 34. The image selector 354 selects the second image information Dg2 input from the second processor 4 and outputs the selected information to the composing unit 32 (Step S15).

The composing unit 32 generates the composed image G2 by superimposing the input second image information Dg2 and textual information Dk1 (Step S16), and the generated composed image G2 is output to the display device 6 (Step S17) and displayed on the display of the display device 6. In the case of receiving the release signal, the control unit 35 causes the recording image generator 36 to first generate release image information from the composed image G2 and then output the generated release image information to the server 7.

The control unit 35 determines whether the next second image information Dg2 has been received from the second processor 4 (Step S18). In a case where the control unit 35 determines that the next second image information Dg2 has been received from the second processor 4 (Step S18: Yes), the control unit 35 returns to Step S15 and continues processing on the next second image information Dg2. In a case where the control unit 35 determines that the next second image information Dg2 has not been received from the second processor 4 (Step S18: No), the compatibility mode control processing is finished.

Figure 4:
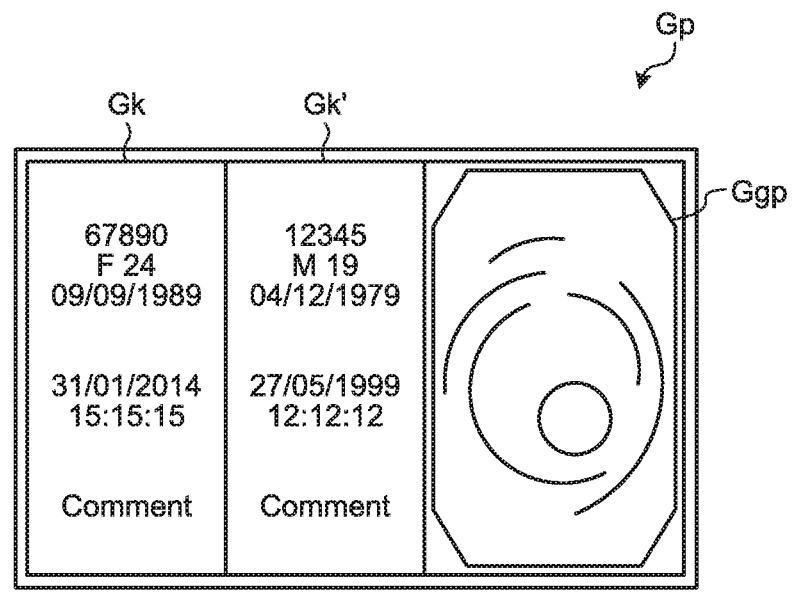
FIG. 4 is a diagram illustrating an exemplary composed image displayed on a display device connected to a conventional processor as a parent device.
Figure 5:
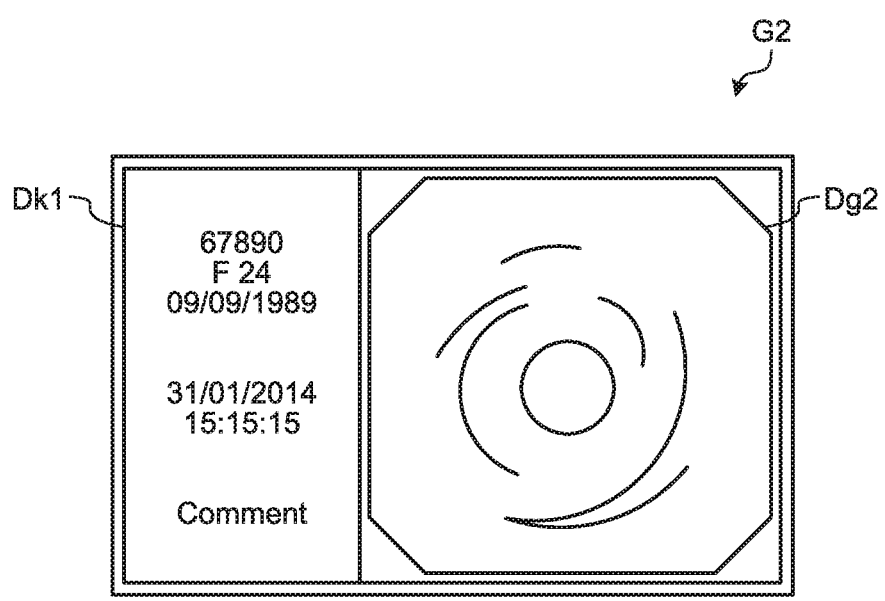
FIG. 5 is a diagram illustrating an exemplary composed image displayed on a display device in the endoscope system according to the first embodiment.

FIG. 4 is a diagram illustrating an exemplary composed image displayed on a display device connected to a conventional processor as a parent device. FIG. 5 is a diagram illustrating an exemplary composed image displayed on a display device in the endoscope system according to the first embodiment. As illustrated in FIG. 4, conventionally, any of the processors regardless of distinction between child and parent devices generates a composed image by superimposing textual information and image information captured by the scope and outputs the generated composed image to the processor as the parent device. Therefore, when a composed image in which image information Ggp and textual information Gk' are superimposed is input into the processor as the parent device from the processor as the child device, the textual image Gk is further superimposed on the input composed information. As a result, conventionally, the display device connected to the parent device has the output of the composed image Gp in which the two pieces of textual information Gk and Gk' being superimposed on the image information Ggp as an observation target. In this case, it is difficult for the user to discriminate which is correct textual information between the two pieces of textual information Gk and Gk' in the composed image Gp, leading to the difficulty in reading necessary information.

In contrast, in the first embodiment, as illustrated in FIG. 5, the control unit 35 transmits the text superimposing unnecessary command Cu from the first processor 3 as the parent device, and causes the second processor 4 as the child device to output solely the second image information Dg2 on which no textual information is superimposed. Subsequently, the control unit 35 then generates the composed image G2 by superimposing solely one piece of textual information Dk1 related to the second image information Dg2 obtained by the textual information acquisition unit 353 on the second image information Dg2 and displays the composed image G2 on the display device 6. In the composed image G2 in which solely one piece of textual information Dk1 is superimposed on the second image information Dg2, other images and a plurality of pieces of textual information are not superimposed on the textual information Dk1 and the second image information Dg2, and thus, the user may properly read necessary information.

As described above, according to the first embodiment, the first processor 3 controls the processing of the image processing unit 31 in accordance with the communication with the second processor 4, making it possible to generate a composed image in which solely the textual information necessary for image information is superimposed and no unnecessary texts or other images are superimposed even in a case where the display device 6 and the recording apparatus are shared with the first processor 3 and the second processor 4. In other words, in the first embodiment, the first processor 3 may generate an appropriate composed image from which the user may read the necessary information, leading to achievement of smooth diagnosis by the user.

First Modification of First Embodiment

Figure 6:
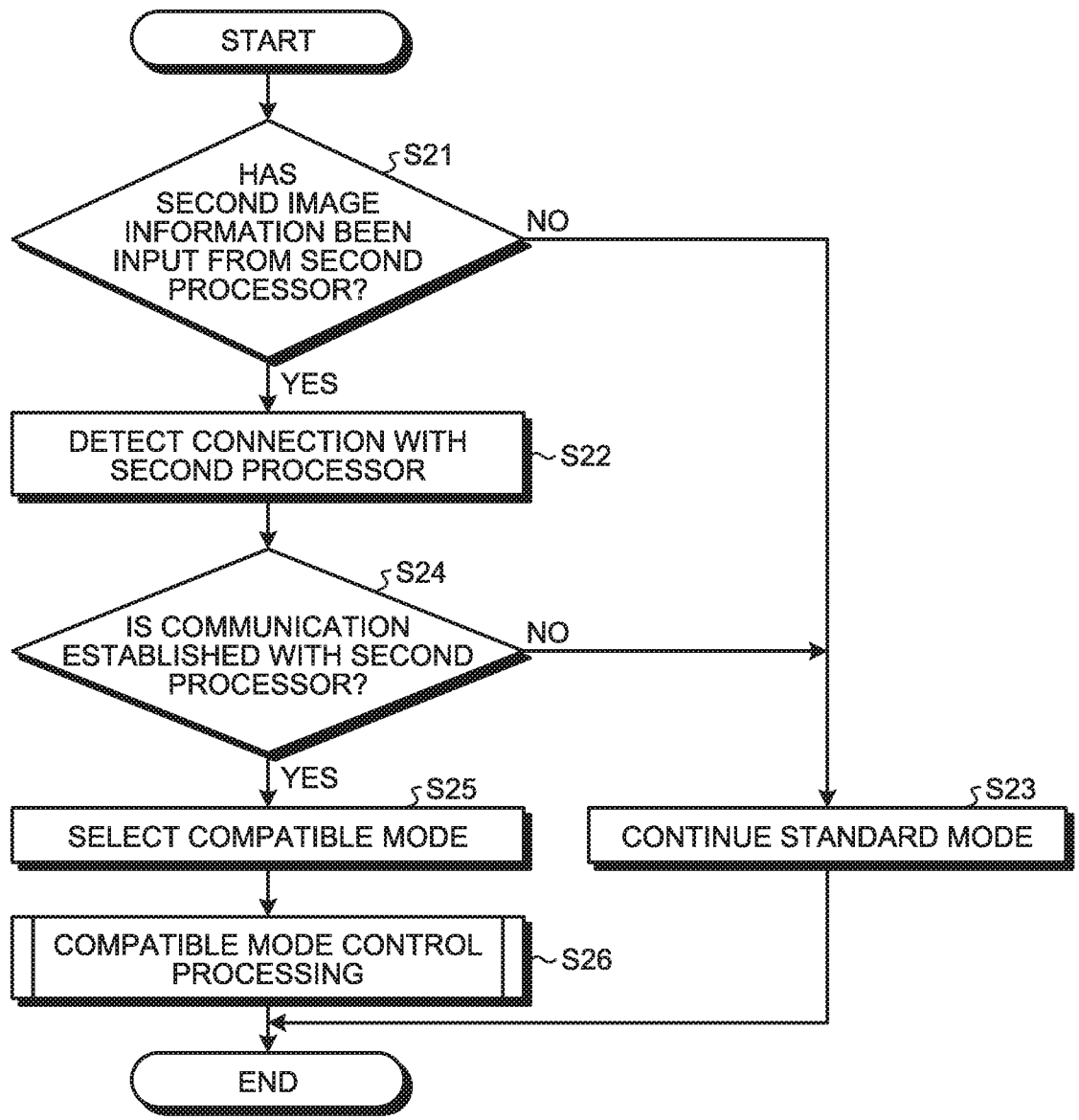
FIG. 6 is a flowchart illustrating setting of a standard mode or a compatible mode by the control unit of the first processor illustrated in FIG. 1 and another processing procedure of control processing of internal processing of the first processor in accordance with individual modes.

FIG. 6 is a flowchart illustrating setting of the standard mode or the compatible mode by the control unit 35 of the first processor 3 and another processing procedure of control processing of internal processing of the first processor 3 in accordance with individual modes.

As illustrated in FIG. 6, the control unit 35 detects the presence or absence of an input of the second image information Dg2 from the second processor 4 into the first processor 3 based on the presence or absence of reception of the second image information Dg2 on the image selector 354 (Step S21). In a case where the control unit 35 detects the input of the second image information Dg2 from the second processor 4 into the first processor 3 (Step S21: Yes), the control unit 35 detects the connection with the second processor 4 (Step S22). Subsequently, the control unit 35 determines whether communication is established between the first processor 3 and the second processor 4 based on a communication result of the communication unit 351 (Step S24). In a case where the control unit 35 does not detect the input of the second image information Dg2 from the second processor 4 into the first processor 3 (Step S21: No) or determines that communication is not established between the first processor 3 and the second processor 4 (Step S24: No), the mode selector 352 continues the standard mode (Step S23). In a case where the control unit 35 determines that communication has been established between the first processor 3 and the second processor 4 (Step S24: Yes), the mode selector 352 selects the compatible mode (Step S25). Step S26 corresponds to Step S5 illustrated in FIG. 2.

As illustrated in the first modification of the first embodiment, it is allowable to configure to cause the first processor 3 to be able to automatically select the compatible mode in a case where the first processor 3 detects the input of the second image information Dg2 by the second processor 4 into the first processor 3 and in the case where the communication is established with the second processor 4.

Second Modification of First Embodiment

Figure 7:
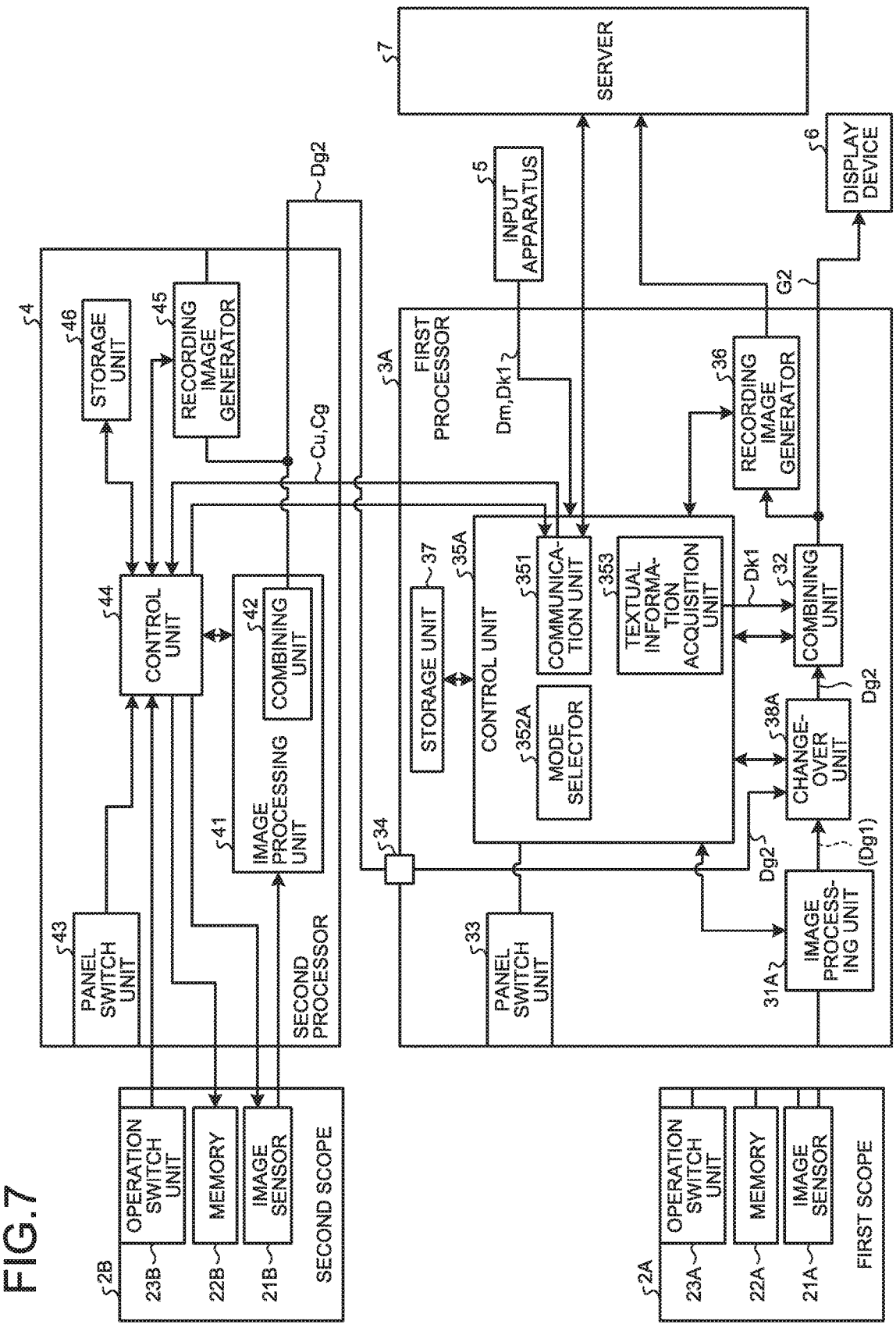
FIG. 7 is a schematic diagram illustrating a general configuration of an endoscope system according to a second modification of the first embodiment.

FIG. 7 is a schematic diagram illustrating a general configuration of an endoscope system according to a second modification of the first embodiment. As illustrated in FIG. 7, a first processor 3A includes an image processing unit 31A and a control unit 35A instead of the image processing unit 31 and the control unit 35 illustrated in FIG. 1, and further includes a changeover unit 38A.

The image processing unit 31A outputs the first image information that has undergone the predetermined image processing to the changeover unit 38A. The control unit 35A has a configuration in which the image selector 354 of the control unit 35 is deleted. Moreover, similarly to the mode selector 352, a mode selector 352A selects one of the standard mode and the compatible mode and causes the changeover unit 38A to switch the image information to be output. The external video image input port 34 inputs the input second image information Dg2 into the changeover unit 38A.

The changeover unit 38A includes an electronic circuit for outputting solely one of the two input signals. Under the control of the mode selector 352A, the changeover unit 38A selects, as the image information to be output to the composing unit 32, the first image information Dg1 input from the image processing unit 31A and the second image information Dg2 input from the external video image input port 34. In a case where the mode selector 352A selects the standard mode, the changeover unit 38A selects and outputs the first image information Dg1. In this case, the composing unit 32 generates a composed image by superimposing the first image information Dg1 and the textual information. In a case where the mode selector 352A selects the compatible mode, the changeover unit 38A selects and outputs the second image information Dg2. In this case, the composing unit 32 generates the composed image G2 by superimposing the second image information Dg2 and the textual information Dk1.

Figure 8:
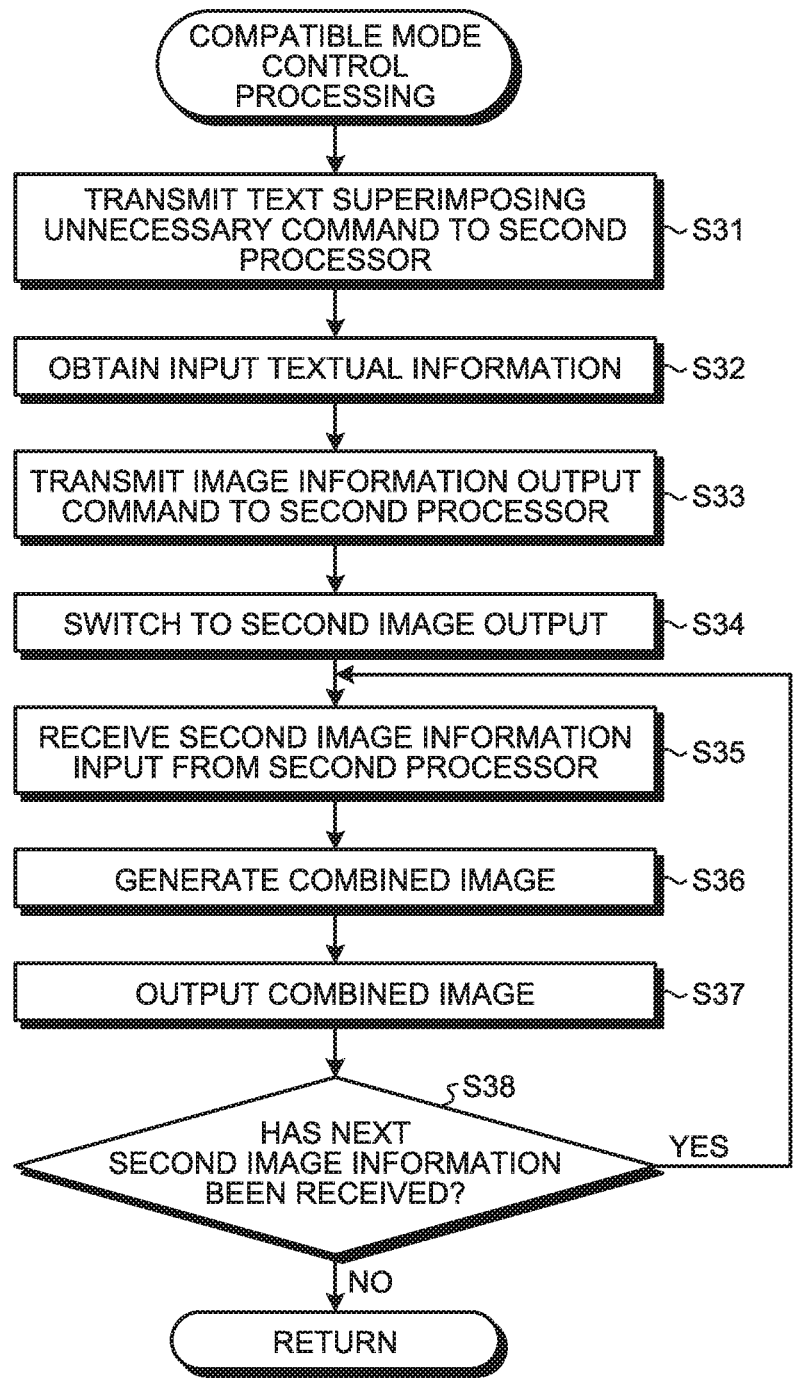
FIG. 8 is a flowchart illustrating a processing procedure of the compatible mode control processing by the control unit of the first processor illustrated in FIG. 7.

The control unit 35A of the first processor 3A performs the processing procedure illustrated in FIG. 2 or 6 and sets the standard mode or the compatible mode. FIG. 8 is a flowchart illustrating the processing procedure of the compatible mode control processing by the control unit 35A of the first processor 3A.

Steps S31 to S33 illustrated in FIG. 8 correspond to Steps S11 to S13 illustrated in FIG. 3, respectively. The mode selector 352A causes the changeover unit 38A to switch the output signal to the second image information Dg2 input from the external video image input port 34 (Step S34). The first processor 3A receives the second image information Dg2 input on the external video image input port 34, from the second processor 4 (Step S35). The received second image information Dg2 is output from the changeover unit 38A to the composing unit 32. Steps S36 to S38 correspond to Steps S16 to S18 illustrated in FIG. 3, respectively. With this configuration, the composing unit 32 generates the composed image G2 by superimposing the second image information Dg2 and textual information Dk1, and the generated composed image G2 is displayed on the display of the display device 6.

As illustrated in the second modification of the first embodiment, it is allowable to switch image information to be output to the composing unit 32 to either the first image information Dg1 or second image information Dg2 using hardware (changeover unit 38A) as a portion of the selector.

Second Embodiment

Figure 9:
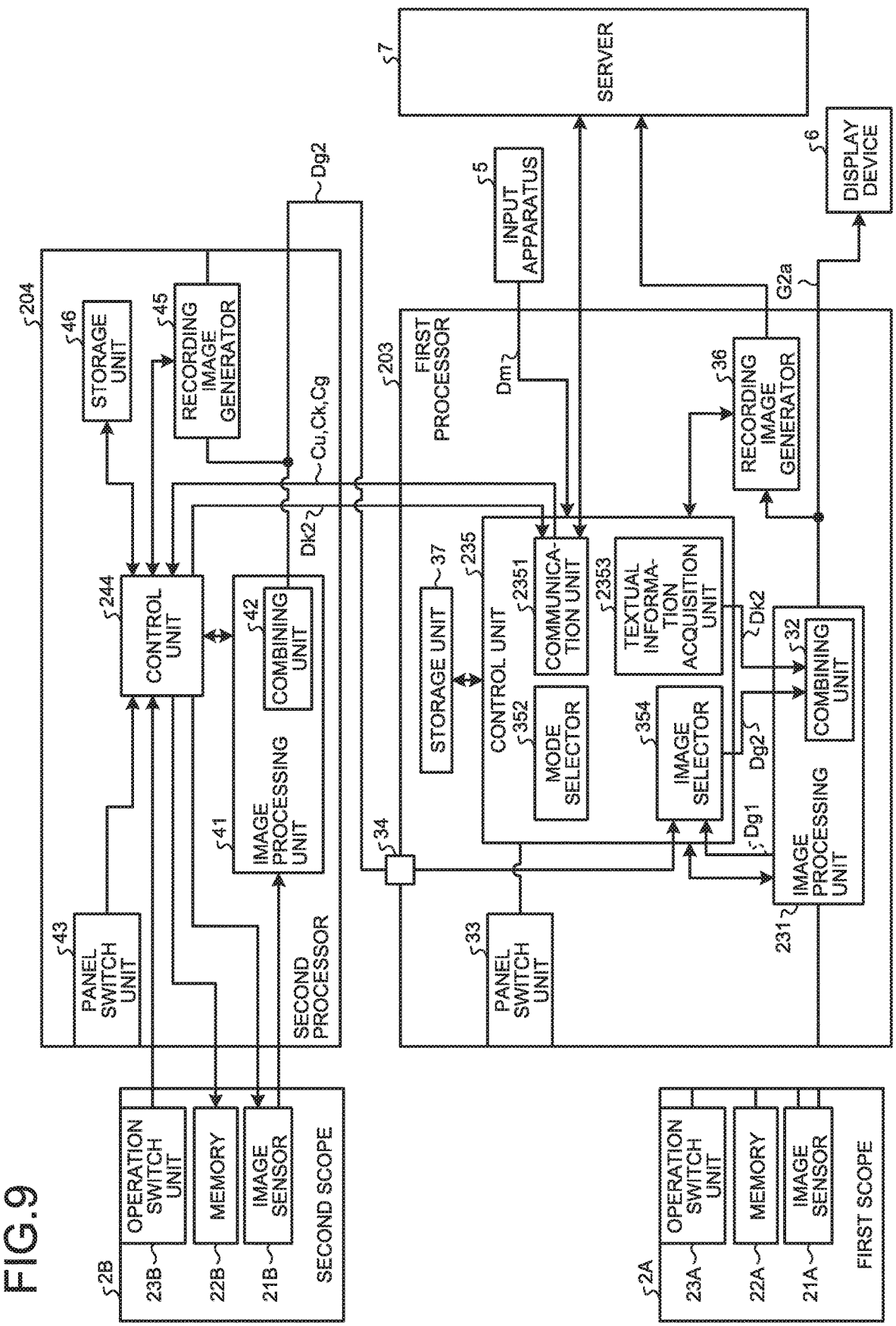
FIG. 9 is a schematic diagram illustrating a general configuration of an endoscope system according to a second embodiment.

Next, a second embodiment will be described. FIG. 9 is a schematic diagram illustrating a general configuration of an endoscope system according to the second embodiment. As illustrated in FIG. 9, the endoscope system according to the second embodiment includes a first processor 203 and a second processor 204.

The first processor 203 includes a control unit 235 having a communication unit 2351 and a textual information acquisition unit 2353. The communication unit 2351 transmits a text superimposing unnecessary command Cu, an image information output command Cg, and an information output command (third command) Ck instructing transmission of textual information Dk2 related to the second image information Dg2 to the image processing unit 41 via a control unit 244 of the second processor 204. The textual information acquisition unit 2353 obtains the textual information Dk2 transmitted from the second processor 204 in response to the textual information output command Ck transmitted from the communication unit 2351 as textual information to be superimposed on the image information to as a composing target. Note that in the second embodiment, solely the scope selection information Dm is input from the input apparatus 5.

The second processor 204 includes the control unit 244. In addition to the second image information Dg2 based on the second imaging signal output from the second scope 2B, the second processor 204 also registers beforehand the textual information Dk2 related to the second image information Dg2, and the control unit 244 transmits the textual information Dk2 to the communication unit 2351 of the first processor 203 in accordance with the textual information output command Ck.

Figure 10:
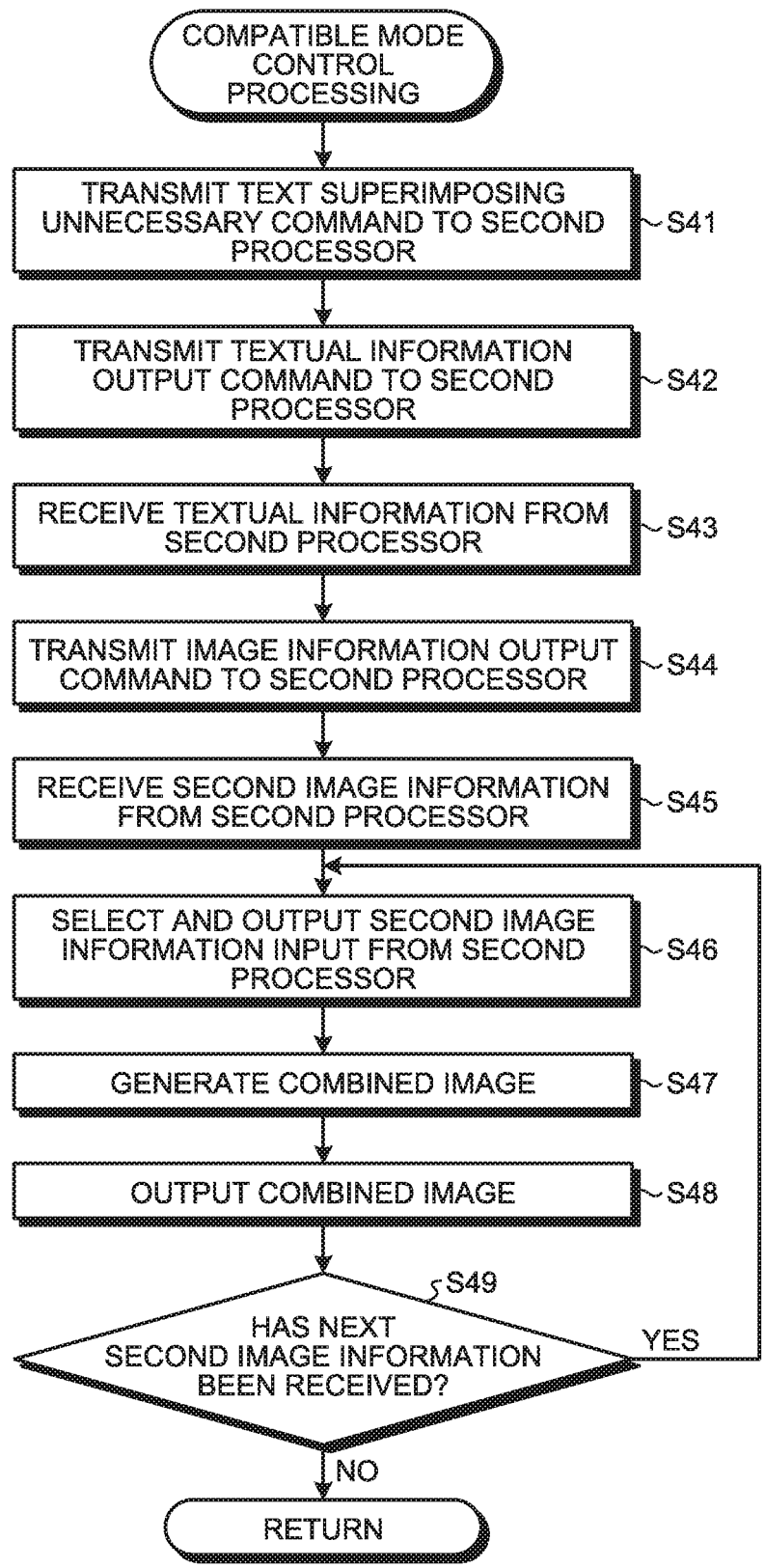
FIG. 10 is a flowchart illustrating a processing procedure of the compatible mode control processing by the control unit of the first processor illustrated in FIG. 9.

The control unit 235 of the first processor 203 sets the standard mode or the compatible mode by performing a processing procedure illustrated in FIG. 2 or 6. FIG. 10 is a flowchart illustrating a processing procedure of compatible mode control processing by the control unit 235 of the first processor 203.

Figure 11:
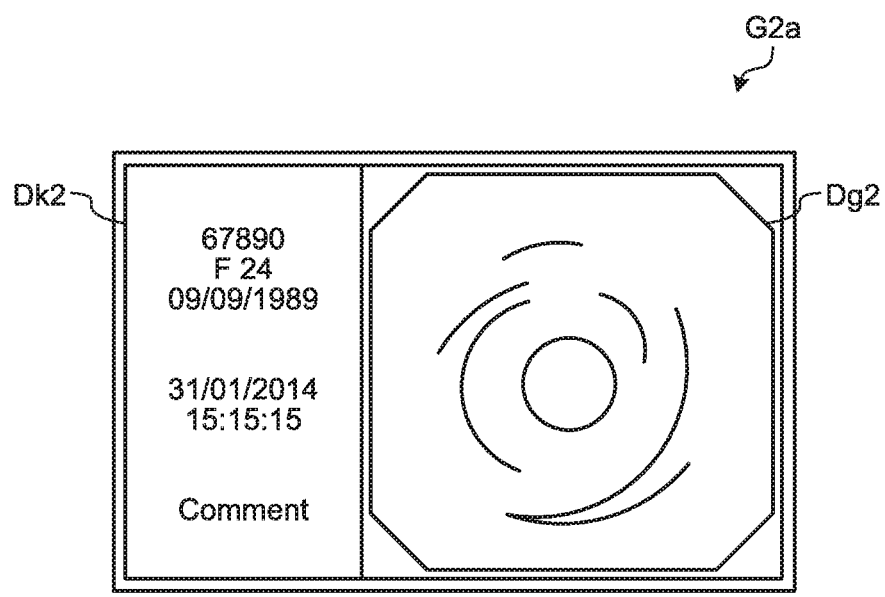
FIG. 11 is a diagram illustrating an exemplary composed image displayed on a display device in the endoscope system according to the second embodiment.

Step S41 illustrated in FIG. 10 corresponds to Step S11 illustrated in FIG. 3. The communication unit 2351 transmits the textual information output command Ck to the second processor 204 (Step S42). In response to the reception of the textual information output command Ck, the second processor 204 outputs the textual information Dk2 from the control unit 244, and then, the control unit 235 receives the textual information Dk2 output from the second processor 204 (Step S43) via the external video image input port 34. Steps S44 to S49 correspond to Steps S13 to S18 illustrated in FIG. 3, respectively. FIG. 11 is a diagram illustrating an exemplary composed image displayed on a display device in the endoscope system according to the second embodiment. By executing the compatible mode control processing illustrated in FIG. 10, a composed image G2a is generated and displayed on the display device 6. The composed image G2a is an image in which only the textual information Dk2 transmitted from the second processor 204 is superimposed on the second image information Dg2 without textual information being superimposed, as illustrated in FIG. 11.

In the second embodiment, the first processor 203 obtains using communication the textual information Dk2 such as patient information registered beforehand in the second processor 204 as a child device, and generates a composed image G2a by superimposing the obtained textual information Dk2 on the second image information Dg2. With this configuration, the second embodiment makes it possible to use the textual information Dk2 once registered in the second processor 204 without registering it again to the first processor 203. Note that, in the second embodiment, the configuration is not limited to the case where the textual information acquisition unit 2353 superimposes the textual information Dk2 transmitted from the second processor 204 on the second image information Dg2 obtained from the second processor 204. It is also allowable to configure such that the textual information Dk2 obtained from the second processor 204 may be superimposed on the first image information generated by the first processor 203. According to this configuration, in the case where there is inspection experience by the second processor 204 in the past and the case of re-inspecting a patient with a patient ID, or the like, being accumulated in the second processor 204 by the first processor 203, it is not necessary to input textual information again on the first processor 203.

First Modification of Second Embodiment

Figure 12:
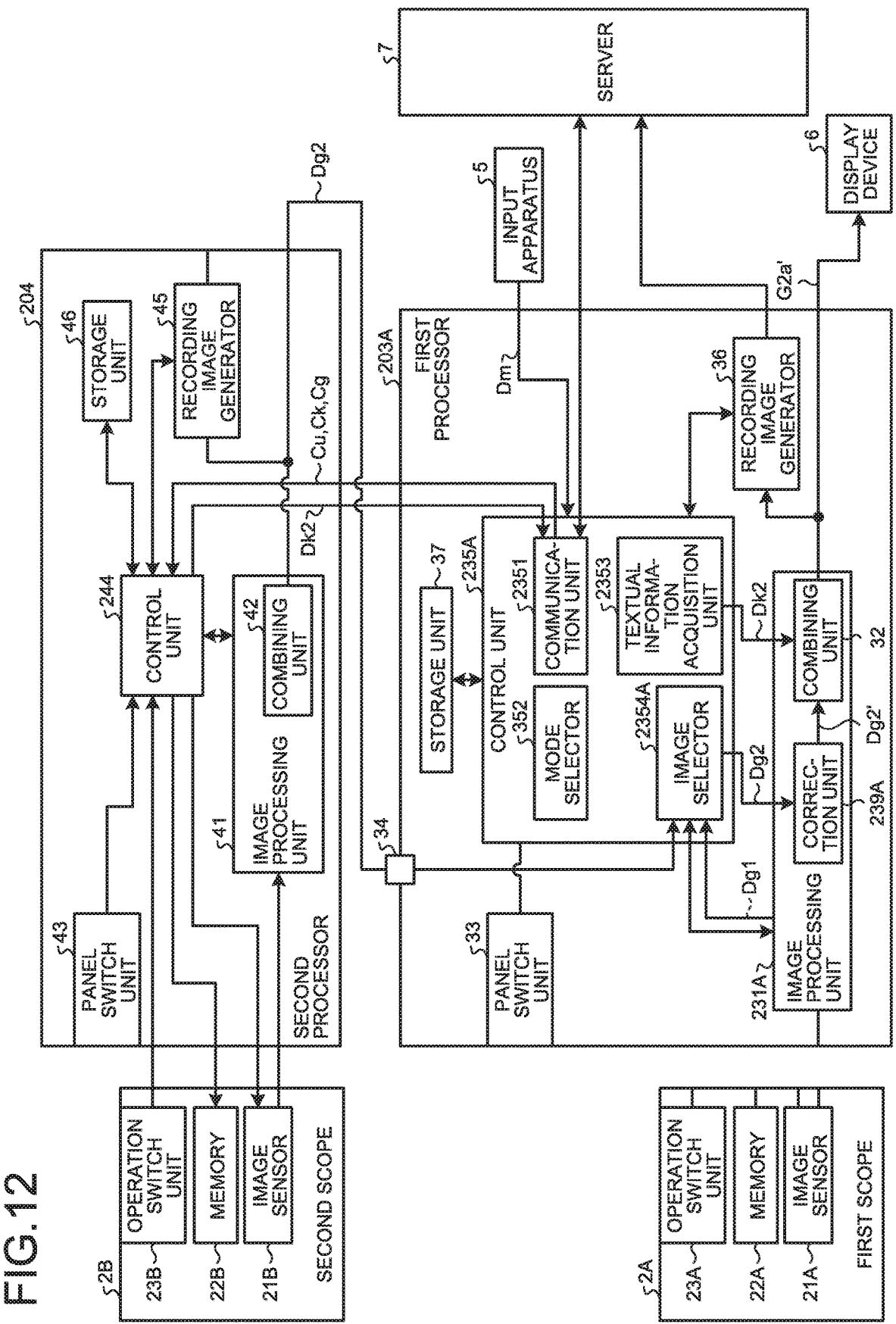
FIG. 12 is a schematic diagram illustrating a general configuration of an endoscope system according to a first modification of the second embodiment.

A first modification of the second embodiment is an exemplary case where in the first processor, the second image information Dg2 obtained from the second processor 204 further undergoes correction processing and then is composed with textual information. FIG. 12 is a schematic diagram illustrating a general configuration of an endoscope system according to the first modification of the second embodiment. As illustrated in FIG. 12, a first processor 203A in the first modification of the second embodiment includes an image processing unit 231A having a correction unit 239A and includes a control unit 235A having an image selector 2354A.

The correction unit 239A performs correction and interpolation processing on the input image information corresponding to the generation of the first processor 203A. Since the first processor 203A is a new generation processor having compatibility with the second processor 204, the first processor 203A may execute upper grade correction processing as compared with the second processor 204.

In a case where the mode selector 352 selects the standard mode, the image selector 2354A outputs the first image information Dg1 to the composing unit 32. In a case where the mode selector 352 selects the compatible mode, the image selector 2354A outputs the second image information Dg2 to the correction unit 239A. The second image information Dg2 undergoes predetermined correction and interpolation processing by the correction unit 239A and then output as second image information Dg2'. The composing unit 32 generates a composed image G2a' by superimposing the second image information Dg2' and the textual information Dk2 related to the second image information Dg2'. As a result, the composed image G2a' having the second image information Dg2' corrected by the correction unit 239A of the first processor 203A is displayed on the display device 6.

The control unit 235A of the first processor 203A sets the standard mode or compatible mode by performing processing procedures illustrated in FIG. 2 or 6. FIG. 13 is a flowchart illustrating a processing procedure of compatible mode control processing by the control unit 235A of the first processor 203A.

Steps S51 to S55 illustrated in FIG. 13 correspond to Steps S41 to S45 illustrated in FIG. 10, respectively. The image selector 2354A selects the second image information Dg2 input from the second processor 204 and outputs the selected information to the correction unit 239A (Step S56). The correction unit 239A performs a predetermined correction processing on the input second image information Dg2 (Step S57). Steps S58 to S60 correspond to Steps S47 to S49 illustrated in FIG. 10, respectively.

As in the first modification of the second embodiment, the first processor 203A may first perform new-generation correction processing on the second image information Dg2 output from the second processor 204 and then may generate the composed image so as to achieve further smooth image confirmation by the user.

Note that in the second embodiment, similarly to the second modification of the first embodiment, the image information to be output to the image processing units 231 and 231A may be converted into the first image information Dg1 or the second image information Dg2 using hardware (changeover unit 38A).

Moreover, while the first and second embodiments are the cases where the second processors 4 and 204 output, as the second image information Dg2, image information generated by performing by the image processing unit 41 predetermined image processing on the second imaging signal (digital) generated by the image sensor 21B, the present disclosure is not limited to this. The second processor 4 and 204 may output the second imaging signal (digital) generated by the image sensor 21B, that is, a signal in the RAW data format as the second image information Dg2 to the control units 35, 35A, 235, and 235A of the first processors 3, 3A, 203, 203A. In a case where the second image information Dg2 in the RAW data format has been input as the image information to be composed from the image selectors 354 and 2354A or the changeover unit 38A to the image processing units 31, 31A, 231, and 231A, the image processing unit 31 first performs predetermined image processing such as OB processing, and then generates a composed image with the textual information Dk1 and Dk2 in the composing unit 32. Moreover, in accordance with instruction information from the input apparatus 5, the control units 35, 35A, 235, and 235A may obtain image information recorded in the past from the storage unit 37 or the database of the server 7 to be connected, and may cause the composing unit 32 to generate a composed image with the textual information Dk1 and Dk2 similarly toward to the obtained image information.

The running programs for individual processing to be executed in the first processors 3, 3A, 203, and 203A, the second processors 4 and 204, and in other units, according to the first and second embodiments, may be recorded on a computer readable recording medium such as a CD-ROM, a flexible disk, a CD-R and a DVD in a form of a file that may be installed or executed, and may be provided. Alternatively, the program may be stored on a computer connected to a network such as the Internet and may be supplied by downloading the program via the network. It is also allowable to provide or distribute the program via a network including the Internet.

According to the present disclosure, it is possible to generate an appropriate composed image from which the user may read necessary information in a case of generating a composed image in which textual information is superimposed on image information input from another signal processing apparatus.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A first signal processing apparatus to which a first endoscope apparatus including a first image sensor is detachably attached, the first signal processing apparatus being communicably connected to a second signal processing apparatus to which a second endoscope apparatus including a second image sensor is attached, the first signal processing apparatus comprising:
  a processor comprising hardware, wherein the processor is configured to:
    execute a composition process comprising generating composed image information in which textual information related to second image information is superimposed on the second image information input from the second signal processing apparatus based on the imaging signal generated by the second image sensor of the second endoscope apparatus; and
    output a first command for instructing the second signal processing apparatus not to superimpose textual information onto the second image information;
    receive, from the second signal processing apparatus, the second image information on which textual information is not superimposed; and
    generate composite image information in which the textual information related to the second image information is superimposed on the received second image information.

2. The first signal processing apparatus according to claim 1,
wherein the processor is configured to:
select either the first image information or the second image information in accordance with the communication with the second signal processing apparatus, the first image information being based on the imaging signal generated by the first image sensor; and
generate a composed image in which image information selected and textual information related to the image information are superimposed.

3. The first signal processing apparatus according to claim 2,
wherein the processor is configured to:
transmit, when communication with the second signal processing apparatus is established, to the second signal processing apparatus the first command and a second command instructing transmission of the second image information to the first signal processing apparatus; and
select the second image information input from the second signal processing apparatus in accordance with the transmission of the second command to the second signal processing apparatus.

4. The first signal processing apparatus according to claim 3,
wherein the processor is configured to receive the textual information related to the second image information from an input device connected to the first signal processing apparatus.

5. The first signal processing apparatus according to claim 3,
wherein the processor is configured to:
transmit to the second signal processing apparatus a third command instructing transmission of the textual information related to the second image information in addition to the first command and the second command; and
generate a composed image in which the second image information selected and the textual information related to the second image information input from the second signal processing apparatus in accordance with the third command are superimposed.

6. The first signal processing apparatus according to claim 2,
wherein the processor is configured to:
perform a correction process on the second image information; and
generate, when the second image information is selected, a composed image in which the second image information and the textual information related to the second image information are superimposed after executing the correction process on the second image information.

7. An endoscope system comprising:
a first signal processing apparatus to which a first endoscope apparatus including a first image sensor is detachably attached; and
a second signal processing apparatus to which a second endoscope apparatus including a second image sensor is attached,
wherein the first signal processing apparatus and the second signal processing apparatus are communicably connected to each other, and
wherein the first signal processing apparatus comprises a processor comprising hardware, wherein the processor is configured to:
execute a composition process comprising generating composed image information in which textual information related to the second image information is superimposed on second image information input from the second signal processing apparatus based on the imaging signal generated by the second image sensor of the second endoscope apparatus;
output a first command for instructing the second signal processing apparatus not to superimpose textual information related to the second image information onto the second image information;
receive, from the second signal processing apparatus, the second image information on which textual information is not superimposed; and
generate composite image information in which the textual information related to the second image information is superimposed on the received second image information.

8. The endoscope system according to claim 7,
wherein the processor is configured to receive the textual information related to the second image information from an input device.

* * * * *